United States Patent
Haas et al.

(10) Patent No.: US 10,600,514 B2
(45) Date of Patent: Mar. 24, 2020

(54) INTUITIVE AUTOMATION IN PATIENT MODELING

(71) Applicants: Varian Medical Systems International AG.; Varian Medical Systems, Inc., Palo Alto, CA (US)

(72) Inventors: Benjamin M. Haas, Brittnau (CH); Thomas Coradi, Lenzburg (CH); Tomasz Morgas, Henderson, NV (US)

(73) Assignees: Varian Medical Systems, Inc., Palo Alto, CA (US); Varian Medical Systems International AG., Cham (CH)

( * ) Notice: Subject to any disclaimer, the term of this patent is extended or adjusted under 35 U.S.C. 154(b) by 298 days.

(21) Appl. No.: 15/596,923

(22) Filed: May 16, 2017

(65) Prior Publication Data

US 2017/0340901 A1    Nov. 30, 2017

Related U.S. Application Data

(60) Provisional application No. 62/342,740, filed on May 27, 2016.

(51) Int. Cl.
| | |
|---|---|
| *G16H 40/63* | (2018.01) |
| *G06T 7/11* | (2017.01) |
| *G06T 7/149* | (2017.01) |
| *G16H 50/50* | (2018.01) |
| *A61N 5/10* | (2006.01) |
| *G06F 3/0488* | (2013.01) |
| *G06F 3/0484* | (2013.01) |

(Continued)

(52) U.S. Cl.
CPC ............ *G16H 40/63* (2018.01); *G06F 19/00* (2013.01); *G06T 7/11* (2017.01); *G06T 7/149* (2017.01); *G16H 50/50* (2018.01); *A61N 2005/1074* (2013.01); *G06F 3/0488* (2013.01); *G06F 3/04815* (2013.01); *G06F 3/04845* (2013.01); *G06F 3/04847* (2013.01); *G06T 3/0068* (2013.01); *G06T 2200/24* (2013.01); *G06T 2207/30096* (2013.01)

(58) Field of Classification Search
CPC ......... G16H 40/63; G06T 7/11; G06T 3/0068; G06F 3/0488; G06F 3/0485; G06F 3/14815; G06F 3/04847
See application file for complete search history.

(56) References Cited

U.S. PATENT DOCUMENTS

2016/0128672 A1\*    5/2016   Kim ..................... A61B 8/466 600/437

\* cited by examiner

*Primary Examiner* — Quoc A Tran (57) ABSTRACT

To overcome the difficulties inherent in conventional treatment planning approaches, new techniques are described herein for providing an intuitive user interface for automatic structure derivation in patient modeling. In an embodiment, a graphical user interface is provided that provides a list of structures of a specified region. The interface uses medical terminology instead of mathematical one. In one or more embodiments, the list of structures may be a pre-defined list of structures that correspond to that region for the purposes of treatment planning. A user is able to actuate a toggle to include and/or exclude each of the structures separately. In one or more embodiments, the user is also able to actuate a toggle to define a perimeter around each included structure, and further define a margin around the perimeter. The user is also able to specify whether the desired output should include a union or the intersection of all included structures.

20 Claims, 4 Drawing Sheets

(51) Int. Cl.
*G06F 3/0481* (2013.01)
*G06T 3/00* (2006.01)
*G06F 17/00* (2019.01)
*G06F 19/00* (2018.01)

Exemplary Computer System 400

Figure 4

INTUITIVE AUTOMATION IN PATIENT MODELING

CLAIM OF PRIORITY

This application claims the benefit of U.S. Provisional Patent Application No. 62/342,740, filed May 27, 2016, entitled "Intuitive Automation in Patient Modeling," which is incorporated herein in its entirety and for all purposes.

COPYRIGHT NOTICE

The patent or application file contains at least one drawing executed in color. Copies of this patent or patent application publication with color drawing(s) will be provided by the Office upon request and payment of the necessary fee.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of this invention relate generally to subject modeling in radiation procedures. More specifically, embodiments of this invention are directed to automated structure derivation in subject modeling.

BACKGROUND OF THE INVENTION

In radiation therapy, accurately identifying and delineating anatomic structures during the treatment planning phase is critically important. The objective of every such procedure is to provide an accurate definition of a target volume and any organs at risk in order to deliver the maximum radiation dose to the target volume (e.g., tumor) while sparing the surrounding healthy tissue from being subject to exposure to potentially harmful radiation.

During the planning stage, a planner often defines specific structures used to control the dose distribution during treatment optimizations. Some of these structures are Boolean or other combinations of targets and/or normal tissues. By defining the intersection of targets and normal tissues as separate structures, different prescription doses and constraints can easily be applied to different regions, facilitating the creation of controlled dose gradients between normal tissues and targets.

To identify and delineate these structures the planner (typically a specialist such as a technician, clinician, or oncologist) reviews one or more images of a target volume in a therapy subject and draws contours within the images that delineate specific volumes and organs at risk. Due to both the importance and the complexities of the process, the delineation and delineation quality check process can take many hours of a planner's time if performed manually. Automatic structure delineation tools have been developed to alleviate some of the burden on the treatment planners. One type of automatic structure delineation is the derivation of structures which is performed by constructing structures based on pre-defined structures, and typically includes defining a sequence of operations that creates an output structure from a set of input structures.

Unfortunately, not all structures can be accurately segmented automatically by the tools that are currently available. Moreover, current treatment planning solutions provide only generic tools for structure derivation that are not optimized for radiation therapy, require mathematical expertise to use properly, and/or are difficult for many radiation oncologists to intuitively understand. Each of these drawbacks increases the likelihood of human error and the potential for harmful radiation to be misdirected. Many conventional tools rely on the creation and usage of Boolean operations (which can be difficult to understand), and on the generation of temporary structures to store intermediate results that are of little to no clinical interest. Some approaches provide only partial functionalities requiring users to switch between tools. Moreover, the same solutions often require significant manual execution and re-application when the input structure(s) are updated, or the underlying data of the input structure(s) change, all of which further presents opportunities to introduce errors or unintended/undesirable outputs.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in conventional treatment planning approaches, new techniques are described herein for providing an intuitive interface for automatic subject modeling that includes structure identification and segmentation. In an embodiment, a graphical user interface is provided that provides a list of structures of a specified region. In one or more embodiments, the list of structures may be a pre-defined list of structures that correspond to that region for the purposes of treatment planning. Via the graphical user interface, a user (such as a clinician, radiation oncologist, or radiation therapy operator, etc.) can actuate one or more toggles to include and/or exclude each of the structures separately. In one or more embodiments, the user is also able to actuate one or more toggles to define a perimeter around each included structure, and further define a margin around the perimeter. The user is also able to actuate one or more toggles to specify whether the desired output should include a union or the intersection of all included (e.g., toggled) structures.

According to another aspect, a method is provided for automatically generating delineated structures, e.g., during patient modeling for the treatment planning phase, for example. In one or more embodiments, a graphical user interface that includes an image of an area of interest is generated and presented (e.g., in a display device) to a user. User supplied input corresponding to a selection of one or more structures is then received. The user supplied input may include, for example, one or more structures from a pre-defined list of structures that correspond to an area of interest displayed in the image. Once the user input phase is completed, the user inputs are submitted, an input image is processed based on the submitted user input, and the structures in the input image selected by the user are automatically contoured and graphically represented directly on a display of the input image.

In still further embodiments, the input image data continues to be monitored such that even when the input image is changed, either manually or with an updated image, the contouring generated from the input supplied by the user persists, adapting to the new image data via automatic propagation. In one or more embodiments, the combination of Boolean operations that are required to be performed to generate the graphical display is performed completely transparently with respect to the user.

Further embodiments provide systems and methods for generating the graphical display of automated contouring based on user supplied input that includes a processor, memory, display device and user input device that collectively perform the execution and implementation necessary to display a user interface comprising a plurality of graphical elements operable to be toggled, receive the user supplied input of one or more actuations of the elements, convert the user supplied input into a corresponding combination of Boolean operations, generate the display, monitor the input image data, and update the output based on modifications to the input image data.

By utilizing the systems and methods described above, target modeling using automatically contoured structures can be performed simply, intuitively, and efficiently to reduce the burden on users in performing manual contouring and to reduce the potential for user-introduced errors.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter:

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIG. 3) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

Exemplary Graphical User Interface

Figure 1:
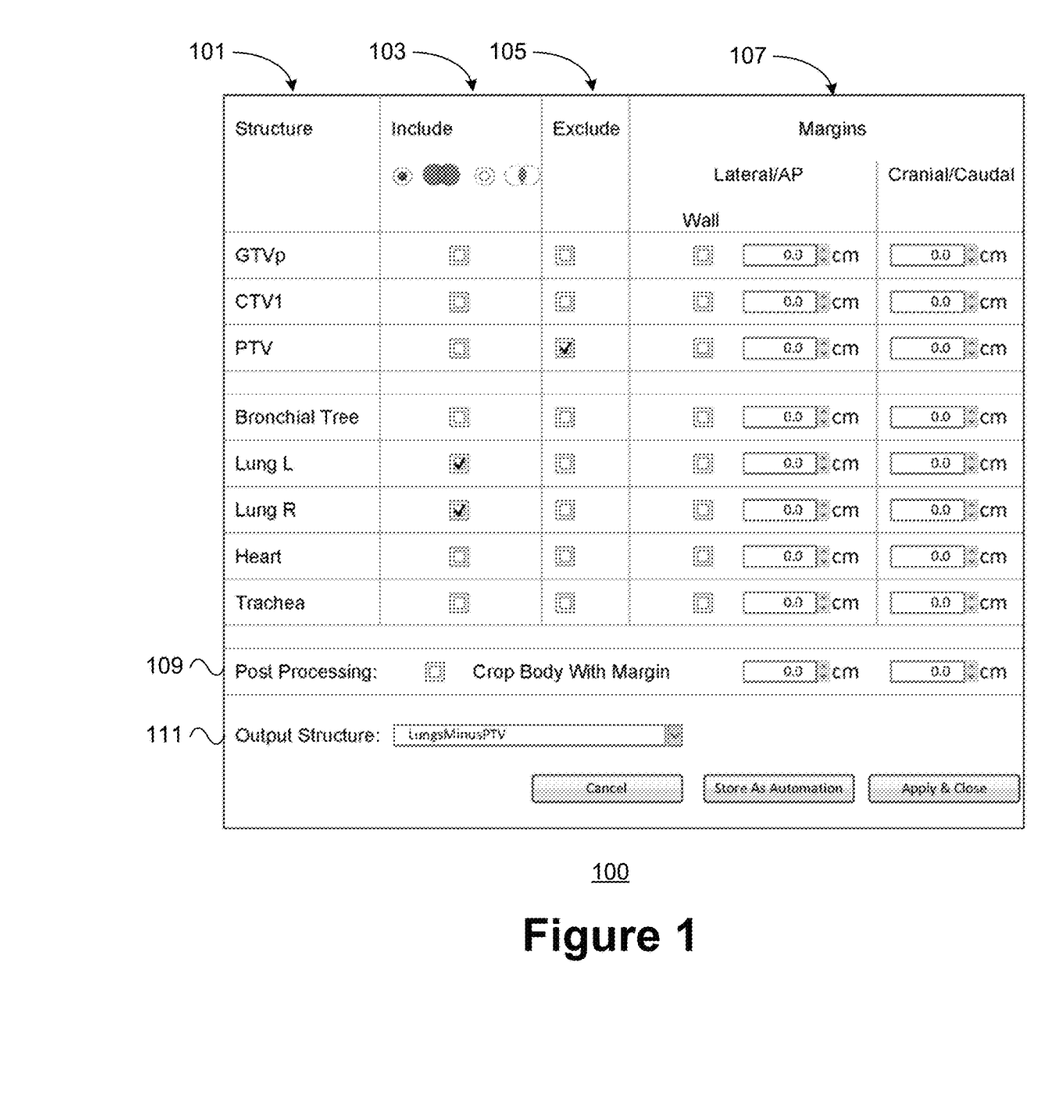
FIG. 1 depicts a first user input portion of an exemplary graphical user interface, in accordance with embodiments of the present disclosure.

FIG. 1 depicts a portion of an exemplary graphical user interface 100, in accordance with one or more embodiments. As depicted, the graphical user interface 100 may be implemented as, for example, a tabular panel used to define automations for a set of structures contained within a contouring (also known as patient modeling) workspace of a treatment planning system. The panel can be shown in a separate dialog or as a graphical window docked right next to the structure list that is already present in a contouring workspace that includes one or more images of a region in a treatment subject.

Compared to other proposed solutions, the claimed subject matter simplifies the process of structure automation and combination substantially, both by the number of steps required and by the time required for a user to understand and learn how to use the tool properly. According to one or more embodiments, all of the operations needed for structure combination and automation is combined in one tool that is easy to learn and understand due to an intuitive user interface design (exemplified by the graphical user interface 100 depicted in FIG. 1), using natural language and medical terms. The graphical user interface is optimized for treatment planning, containing exactly the set of operations necessary to perform clinical tasks, without the need to create temporary structures to hold intermediate results.

In one or more embodiments, in contrast to conventional approaches with interfaces that use advanced mathematical symbols or technical terms, implementations of the graphical user interface are expressed (e.g., displayed to the user) using natural language, medical (anatomical) terminology and/or easy to understand graphical icons to describe and/or label operations. Natural language may include, for example, relative orientation or directions (e.g., left, right, top, bottom, etc.), anatomical designations (e.g., anterior, medial, lateral, cranial, posterior, etc.), and geometric axis characteristics (e.g., union, intersection, includes, excludes).

Implementations of the user interface also use a simplified functional range that corresponds to what is used by physicians in clinical use cases, such as Boolean structures and skin sparing. Rather than expressing functionality mathematically, or supporting all possible solutions, in one or more embodiments the user interface presents only (pre-determined) clinically relevant input and output options to the user from which the user can select. These options may represent only the clinically relevant operations involving existing structures. As depicted in FIG. 1, the display of the graphical output may use a tabular representation, instead of or in addition to graphs, flow charts, or formulas, and can include multiple structures without the need or understanding of advanced modes that include formulas and order of operations.

Displays of the list of structures already known to the user from the patient modeling workspace can also be reused, so the claimed subject matter can be completely integrated in contouring screen layouts, allowing for immediate visualization of results and the automatic execution of sequences assigned to output structures when input structures are ready (as indicated by a special user interface element) and cleared when input structures are changed.

As depicted in FIG. 1, a graphical user interface 100 is provided that provides a list of structures (e.g., presented in column 101) of a specified region. The list may be populated from, for example, a knowledge base (such as a repository) of data that may be storing previously defined structures by the user or user peers or are even standardized within the industry and remotely accessible to the graphical user interface (e.g., as part of, or communicatively coupled to, an application instantiating the graphical user interface). The region may be pre-identified as or pre-associated with the region or area being displayed in a display of image data. The list of structures may be a pre-defined list of structures that correspond to that region for the purposes of treatment planning, or a partial list of structures (e.g., organs) in the region associated with the image data and pre-determined to be of particular significance or having a frequency of interest above a threshold, or a comprehensive list of structures in surrounding areas or within a system/organism.

In one or more embodiments, the region itself may be alternately automatically selected, manually selected, and manually changed based on further user input. Via the graphical user interface, a user (such as a clinician, radiation oncologist, or radiation therapy operator, etc.) can actuate a toggle to include and/or exclude each of the structures separately (e.g., via user-interface elements in columns 103 and 105 of the graphical user interface 100 in FIG. 1). In some instances, specifically delineating the tissue wall of a structure from the underlying tissue can be of clinical interest. According to such embodiments, the user is also able to define walls around each included structure using surface contours of the underlying structure. As depicted in FIG. 1, for example, the sub-column within column 107 may be used to integrate and incorporate the creation of the perimeter or "wall" margin structures from surface contours.

According to one or more embodiments, via the graphical user interface, multiple structures can be included for one or yore operations or displays within a single operation mode. In contrast to typical approaches that often require using an "advanced" mode to include multiple structures to perform structure automation operations (typically by using formulas and parentheses), embodiments of the present claimed invention present a graphical display of a table of clinically relevant inputs, outputs, and operations that represent a subset of possible formulas that can be performed by the structure automating tool. According to various embodiments, the user is also able to actuate a toggle (e.g., via user-interface elements in row 109 of the graphical user interface 100 in FIG. 1) to specify whether the desired output should include a union or the intersection of all included structures.

Once the user input phase is completed, the user input received via the graphical user interface is submitted (e.g., to an image rendering application executed by a graphics processor), an input image is processed by a graphics processor, and contouring of the structures in the input image selected by the user is automatically and immediately performed, rendered, and graphically represented directly on a display of the input image, or overlapping visually on a display of the input image. In one or more embodiments, the automatically generated contours include the area contained in the margins specified by the user. In still further embodiments, the input image data continues to be monitored such that even when the input structures are changed, either manually or with an updated structural delineation, the contouring generated from the input supplied by the user persists, and is graphically adapted by the processor to the new image data via automatic propagation for immediate visualization.

Optionally, the user is able to store one or more contoured structures from the selection of one or more toggles for future use or reference. For example, the output from generating contouring based on the user input that includes two or more structures can be stored as a new structure, and the resultant structure can be saved through the user interface at row 111. As depicted in FIG. 1 for example, a user is able to define the file/data storage element of the output. In one or more embodiments, the combination of Boolean operations that is required to be performed to generate the graphical display is performed completely transparently with respect to the user, and the output structure corresponding to the user input may be further specified by the user (e.g., via user-interface elements in row 111 of the graphical user interface 100 in FIG. 1). According to further embodiments, the output structure may thereafter be referenced by an integrated patient modeling workspace. In still further embodiments, the integrated patient modeling workspace may include functionality to perform and/or display structure contouring.

The example features shown in FIG. 1 are provided for illustrative purposes and is not to be construed as limiting. More or fewer elements (as well as different arrangements of those elements) than are shown in FIG. 1 may be implemented in other embodiments. Further, the features described with respect to FIG. 1 (specifically graphical element 100) do not necessarily appear in all embodiments of the presently described innovations.

Figure 2:
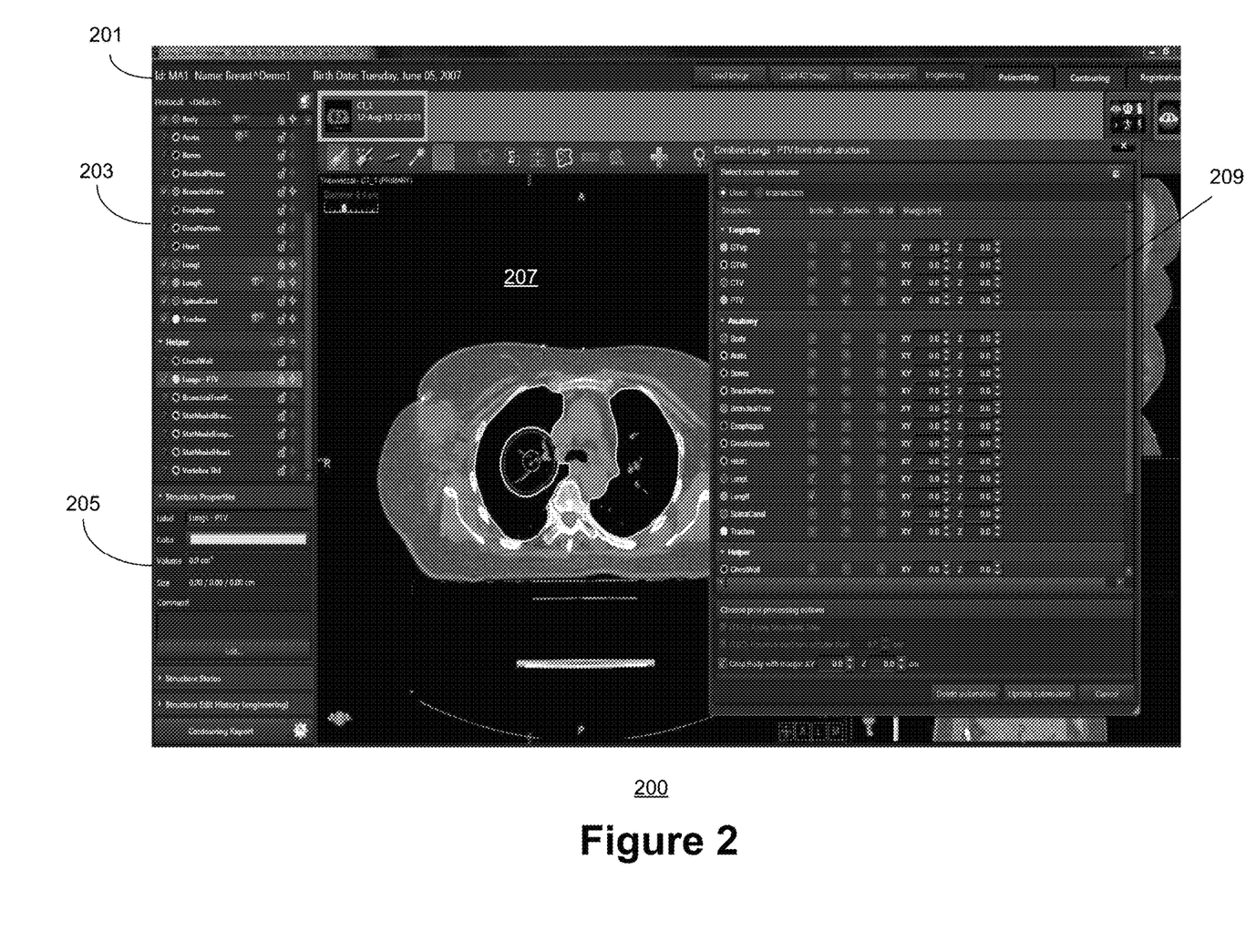
FIG. 2 depicts an exemplary graphical user interface, in accordance with embodiments of the present disclosure.

FIG. 2 depicts a screen capture of exemplary graphical user interface 200 illustrating an example automatic structure contouring. As shown in FIG. 2, a computer generated image of one or more structures in a treatment subject may be displayed in a window, e.g., image window 207. A user may be displayed an identification of a radiation (treatment) subject at element 201 that includes an identification of the subject (e.g., MA1), a name of the procedure or program (e.g., Name: Breast^Demol), and additional information (e.g., age) of the subject that may be immediately pertinent to the user (e.g., clinician, oncologist, radiologist). As depicted in FIG. 2, the structure derivation interface 200 may also include a depiction of the current parameters (e.g., parameter list 203) applied to the structures in the image presented in image window 207. In one or more embodiments, the parameter list 203 may be pre-populated with all or substantially all possible structures identified in the image displayed in image window 207. These structures may be manually identified by a user through the graphical user interface 200, automatically by referencing images with pre-labeled structures, or a combination of both.

Optionally, structure derivation interface 200 could also include a structure property window (e.g., structure property window 205), that allows a user to configure the parameters applied to the image in image window 207 and displayed in parameter list 203. For example, one or more of the color, size, or volume of a specific structure may be configured in structure property window 205. In one or more examples, the particular structure being configured may be selected using a drop down menu populated by the structures in the parameter list 203. The image window 207 may display one or more structures of a target area imaged using an imaging system and generated by one or more processors in a computing system. In one or more embodiments, the imaging system may be implemented according to one or more of any number of imaging modalities including, but not limited to: radiography, magnetic resonance imaging (MRI), ultrasound, elastography, photoacoustic imaging, thermography, tomography, echocardiography, spectroscopy, and molecular imaging (e.g., positron emission tomography). As depicted in FIG. 2, the target area is imaged as a CT scan of a bi-section of a subject's respiratory system. In one or more embodiments, the planning target volume (PTV) that includes the clinical target volume (CTV) and one or more gross tumor volumes (GTV) may be separately identified, delineated (contoured), and displayed in the image window 207.

Exemplary structure configuration window 209 depicts a graphical user sub-interface with functionality similar to the user-interface described above with respect to FIG. 1, including the functionality to specifically include or exclude contouring for any number of structures appearing in the target area displayed in the image window 207. Other functionality may include, but is not limited to, contouring a perimeter (e.g., a wall) and/or a margin around a perimeter of one or more structures. Optionally, post processing features may be selected in structure configuration window 209. In one or more embodiments, each time user input (e.g., a user selection or toggled element) is received through structure configuration window 209, the parameter list 203 is updated to reflect the change, and the target area displayed in image window 207 is updated to apply the user input. For example, if a user selects the toggle for including a structure from the pre-defined list of structures, the image in image window 207 of the target area is dynamically updated to include contouring for the corresponding structure. Likewise, if a user selects the toggle to exclude a structure from the pre-defined list of structures, the image in image window 207 of the target area is dynamically updated to remove any contouring present for the corresponding structure. In either case, the parameter list 203 is similarly updated to reflect included (and/or excluded) structures based on the user input received.

The example features shown in FIG. 2 are provided for illustrative purposes and is not to be construed as limiting. More or fewer elements (as well as different arrangements of those elements) than are shown in FIG. 2 may be implemented in other embodiments. Further, the features described with respect to FIG. 2 (specifically graphical element 200) do not necessarily appear in all embodiments of the presently described innovations.

Automatic Structure Derivation

Figure 3:
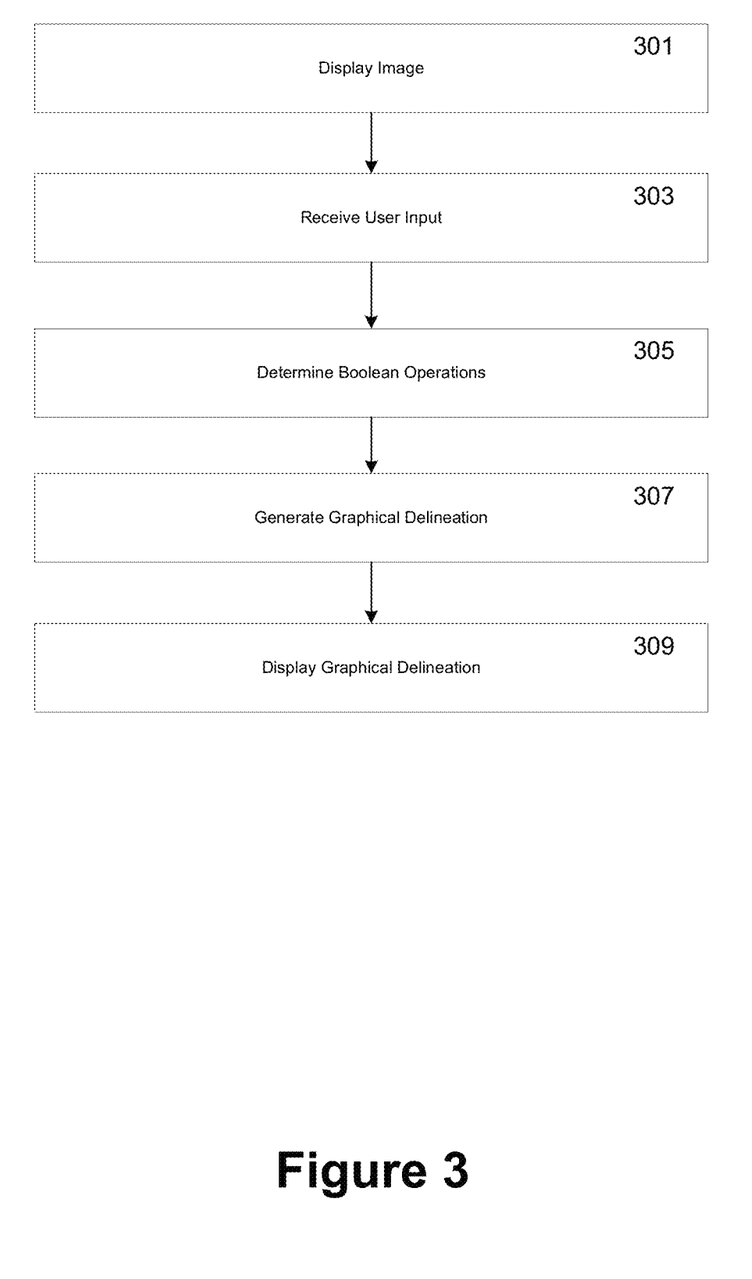
FIG. 3 depicts a flowchart for performing automatic contouring, in accordance with embodiments of the present disclosure.

FIG. 3 depicts a flow chart illustrating an example process performed by a computer system implementing automatic structure segmentation (e.g., structure contouring), according to embodiments of the claimed subject matter. The process described with respect to FIG. 3 may be performed by any of the one or more computing systems described with respect to FIG. 4. For example, in some embodiments, some or all of the steps of described process 300 are performed by any of a computing system operating as part of a treatment planning system, or patient modeling system. The process flow illustrated in FIG. 3 is provided for illustrative purposes only. Those skilled in the art will understand that one or more of the steps of the process illustrated in FIG. 3 may be removed or the order of the steps may be changed.

The process depicted in FIG. 3 can optionally begin at step 301 through the display of an image in a display device. In one or more embodiments, the image may comprise at least a target area in a treatment subject that includes at least one of a planning target volume (PTV), a clinical target volume (CTV), and/or a gross tumor volume (GTV). According to one or more embodiments, the image may be displayed in an image window, such as image window 207 of a graphical user interface, such as graphical user interface 200, each described above with respect to FIG. 2. The image may be computed from imaging data taken according to one or more imaging modalities, and may be graphically rendered by one or more (graphics) processors in a computing system communicatively coupled to the display device.

The process continues at step 303 by receiving user input. User input, may be received through, for example, at least a portion of a graphical user interface (e.g., user interface 100, structure configuration window 209). In one or more embodiments, the user input may consist of a user actuation of one or more toggles corresponding to one or more structures in a pre-defined list of structures displayed in the image at step 301. Optionally, the user input may include the actuation of one or more toggles corresponding to a perimeter and/or margins corresponding to the one or ore structures. Optionally, the user input may also include the actuation of one or more toggles corresponding to a user selection of the display of an intersection or union of other user-selected elements. In one or more embodiments, each user input received in the graphical user interface causes the performance of steps 303-309, with those steps being repeated each time an additional user input is received. Alternatively, user input can be collected (and graphically represented to the user) temporarily until a subsequent, user-initiated submission of all user input (e.g., via a submit graphical button), with steps 305-309 being performed in response to the submission.

The process continues at step 305 with calculating and determining any number of a plurality of Boolean operations corresponding to the user input received. For example, a Boolean operation may be generated that corresponds to the union of each structure indicated by the user input for inclusion. In one or more embodiments, the generated Boolean operation is automatically determined and calculated without further input from the user. Optionally, the resultant Boolean operation may be graphically displayed in the graphical user interface to the user (e.g., as a string or mathematical expression). The process continues at step 307 with processing the graphical contouring and automatic segmentation according to the Boolean operation(s) generated at step 305. In one or more embodiments, the graphical contouring may be performed by referencing and comparisons to previously rendered structures in a knowledge base or repository of treatment planning volumes, mapping the target area in the image window to corresponding areas, extrapolating pre-contoured effects to the structures in the target area, and adapting the effects to corresponding specifically to the structures. In one or more embodiments, such adaptation may be performed by, for example, a deformation mechanism or similar mapping and means for automatic propagation.

The process continues at step 309 with updating the image displayed in the graphical user interface (e.g., image window 207 of FIG. 2) with the contouring and delineation effects generated at step 307. In one or more embodiments, updating the image may be performed by one or more graphical processors in a computing system communicatively coupled to the display device. Steps 303-309 may be performed every time user input is received in the graphical user interface. Optionally, steps 305-309 may also be performed automatically without user-input whenever the image data itself is updated or modified (e.g., during real-time imaging monitoring, or updated image sources).

Exemplary Computer System

Figure 4:
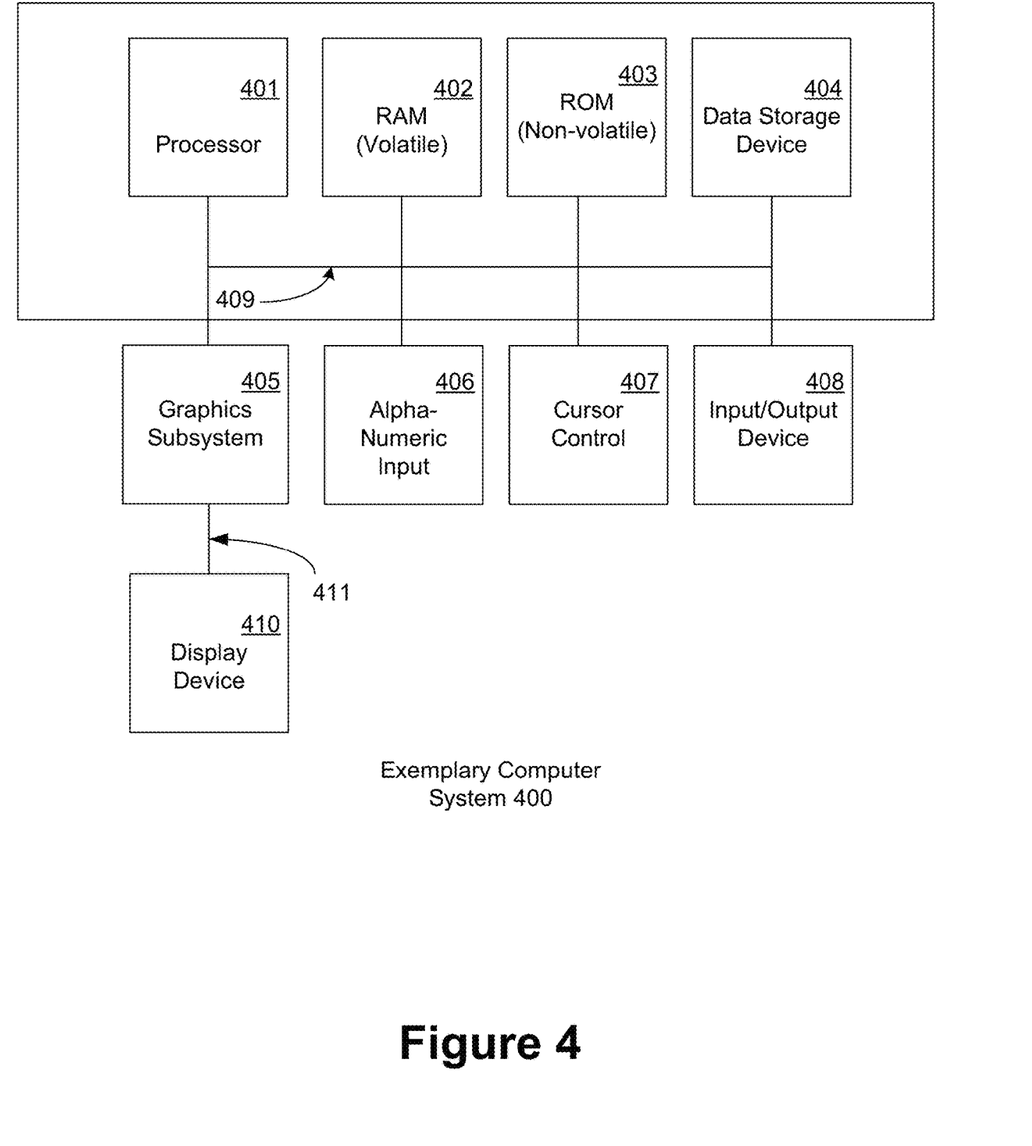
FIG. 4 depicts an exemplary computing environment, in accordance with embodiments of the present disclosure.

In one or more embodiments, structure derivation may be executed as a series of programmed instructions executed on a computing environment described above with respect to FIG. 3. FIG. 4 depicts such a computing environment, including computing system 400 upon which embodiments of the present invention may be implemented includes a general purpose computing system environment. In its most basic configuration, computing system 400 typically includes at least one processing unit 401 and memory, and an address/data bus 409 (or other interface) for communicating information. Depending on the exact configuration and type of computing system environment, memory may be volatile (such as RAM 402), non-volatile (such as ROM 403, flash memory, etc.) or some combination of the two.

The computer system 400 may also comprise an optional graphics subsystem 405 for presenting information to the radiologist or other user, e.g., by displaying information on an attached display device 410, connected by a video cable 411. In one or more embodiments, one or more of the graphical user interfaces described above with respect to FIGS. 1 and 2 may be rendered at least in part in optional graphics subsystem 405. Alternatively, the graphical user interfaces may be rendered at least in part in processing unit 401. According to embodiments of the present claimed invention, the graphics subsystem 405 may be coupled directly to the display device 410 through the video cable 411. In alternative embodiments, display device 410 may be integrated into the computing system (e.g., a laptop or netbook display panel) and will not require a video cable 411. In one or more embodiments, one or more of the graphical user interfaces described above with respect to FIGS. 1 and 2 may be displayed to a user in display device 410.

According to one or more embodiments, one or more of the storage of clinical data and the performance of the automatic structure derivation may be performed in one or more (distributed) computing systems remotely positioned relative to a display device upon which one or more instances of the graphical user interface described above is instantiated. For example, processing may be performed in one or more cloud computing centers using dynamically provisioned resources, with resulting displays presented in a local display and computing device of a user. Likewise, clinical data may be stored in one or more data stores which can be remotely positioned with respect to one or both of the local display and computing device of the user and the computing device performing the bulk of the processing for the automatic structure segmentation and the analysis of the clinical data.

Additionally, computing system 400 may also have additional features/functionality. For example, computing system 400 may also include additional storage (removable and/or non-removable) including, but not limited to, magnetic or optical disks or tape. Computer storage media includes volatile and nonvolatile, removable and non-removable media implemented in any method or technology for storage of information such as computer readable instructions, data structures, program modules or other data. RAM 402, ROM 403, and external data storage device 404 are all examples of computer storage media.

Computer system 400 also comprises an optional alphanumeric input device 406, an optional cursor control or directing device 407, and one or more signal communication interfaces (input/output devices, e.g., a network interface card) 408. Optional alphanumeric input device 406 can communicate information and command selections to central processor 401. Optional cursor control or directing device 407 is coupled to bus 409 for communicating user input information and command selections to central processor 401. Signal communication interface (input/output device) 408, also coupled to bus 409, can be a serial port. Communication interface 408 may also include wireless communication mechanisms. Using communication interface 408, computer system 400 can be communicatively coupled to other computer systems over a communication network such as the Internet or an intranet (e.g., a local area network).

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A method of automatic structure delineation, the method comprising:
   causing display, by a computer system, of an image from medical image data;
   causing display, by the computer system, of a graphical user interface, the graphical user interface comprising a list of structures corresponding to an area of interest displayed in the image and one or more operations available to be performed;

receiving user supplied input through the graphical user interface, the user supplied input corresponding to a selection of structures from the list of structures;

determining and performing a Boolean operation based on the user supplied input, wherein the Boolean operation comprises a union of or an intersection of each structure of the selection of structures indicated by the user supplied input for inclusion in the Boolean operation;

generating a graphical delineation of the structures resulting from the Boolean operation;

storing the graphical delineation as one or more corresponding output structures; and updating the display to include the graphical delineation of the one or more output structures.

2. The method according to claim 1, wherein the list of structures comprises a pre-determined list of structures determined to be clinically relevant by analyzing clinical data corresponding to the area of interest.

3. The method according to claim 1, wherein the user supplied input comprises actuation of a toggle in the graphical user interface to include the selection of structures.

4. The method according to claim 3, wherein the user supplied input further comprises actuation of a toggle in the graphical user interface to define a wall of a structure of the selection of structures.

5. The method according to claim 4, further comprising analyzing clinically relevant data corresponding to the area of interest to reference one or more surface contours corresponding to the structure, wherein the wall of the structure is defined using the one or more surface contours corresponding to the structure.

6. The method according to claim 4, wherein the user supplied input further comprises actuation of a set of parameters displayed in the graphical user interface that correspond to a margin around the wall.

7. The method according to claim 1, further comprising:
monitoring subsequent user supplied input to detect a modification to a structure of the selection of structures;
automatically propagating the graphical delineation to correspond to the modification; and
updating the display to include the modification.

8. The method according to claim 1,
wherein the user supplied input comprises at least one of: selection of a structure in the list of structures, and deselection of a structure in the list of structures,
wherein the selection of a structure comprises a display of a union of the selected structure and the selection of structures,
further wherein the deselection of a structure comprises a display that does not include the deselected structure.

9. The method according to claim 1, wherein the graphical user interface displays the list of structures and the one or more operations in a tabular representation.

10. The method according to claim 1, further comprising referencing the one or more output structures in a patient modeling workspace.

11. A system comprising:
a memory device configured to store a set of programmed instructions and image data;
a user input device configured to receive user supplied input;
a display device configured to display a graphical user interface; and
a processor configured to execute the programmed instructions to generate a display of the graphical user interface comprising a display of an image corresponding to the image data and a display of a list of structures corresponding to an area of interest in the image and one or more operations available to be performed, the processor being further configured to receive user supplied input from the user input device corresponding to a selection of structures from the list of structures, to determine and perform a Boolean operation based on the user supplied input, wherein the Boolean operation comprises a union of or an intersection of each structure of the selection of structures indicated by the user supplied input for inclusion in the Boolean operation, to generate a graphical delineation of the structures resulting from the Boolean operation, to store the graphical delineation as one or more corresponding output structures, and to update the image to include the graphical delineation in the display.

12. The system according to claim 11, wherein the list of structures comprises a pre-determined list of structures determined to be clinically relevant by analyzing clinical data corresponding to the area of interest.

13. The system according to claim 11, wherein the user supplied input comprises actuation of a toggle displayed in the graphical user interface to include the selection of structures.

14. The system according to claim 13, wherein the user supplied input further comprises actuation of a toggle displayed in the graphical user interface to define a perimeter around the selection of structures.

15. The system according to claim 14, wherein the user supplied input further comprises actuation of a set of parameters displayed in the graphical user interface that correspond to a margin around the perimeter.

16. The system according to claim 11, wherein the processor is further operable to monitor subsequently received user supplied input to detect a modification to a structure of the selection of structures, automatically propagate the graphical delineation to correspond to the modification; and update the image to include the modification.

17. The system according to claim 11,
wherein the user supplied input comprises at least one of: selection of a structure in the list of structures, and deselection of a structure in the list of structures,
wherein the selection of a structure comprises a display of a union of the selected structure and the selection of structures,
further wherein the deselection of a structure comprises a display that does not include the deselected structure.

18. A non-transitory computer readable medium comprising a plurality of programmed instructions which, when executed by a processor in a computing system, is operable to implement automatic structure delineation, the computer readable medium comprising:
instructions to cause display of an image from medical image data;
instructions to cause display of a graphical user interface comprising a list of structures corresponding to an area of interest displayed in the image and one or more operations available to be performed;
instructions to receive, as input, user supplied input corresponding to a selection of structures from the list of structures;
instructions to determine and perform a Boolean operation based on the user supplied input, wherein the Boolean operation comprises a union of or an intersection of each structure of the selection of structures indicated by the user supplied input for inclusion in the Boolean operation;

instructions to generate a graphical delineation of the structures resulting from the Boolean operation;

instructions to store the graphical delineation as one or more corresponding output structures; and instructions to update the image with the graphical delineation of the selected structures.

19. The non-transitory computer readable medium according to claim 18, wherein the list of structures comprises a pre-determined list of structures determined to be clinically relevant by analyzing clinical data corresponding to the area of interest.

20. The non-transitory computer readable medium according to claim 18, wherein the user supplied input comprises a user actuation of at least one of:

a toggle displayed in the graphical user interface and operable to include the selection of structures;

a toggle displayed in the graphical user interface and operable to define a wall of a structure of the selection of structures; and a set of parameters displayed in the graphical user interface and corresponding to a margin around a wall of a structure of the selection of structures.

* * * * *